Figure 1:
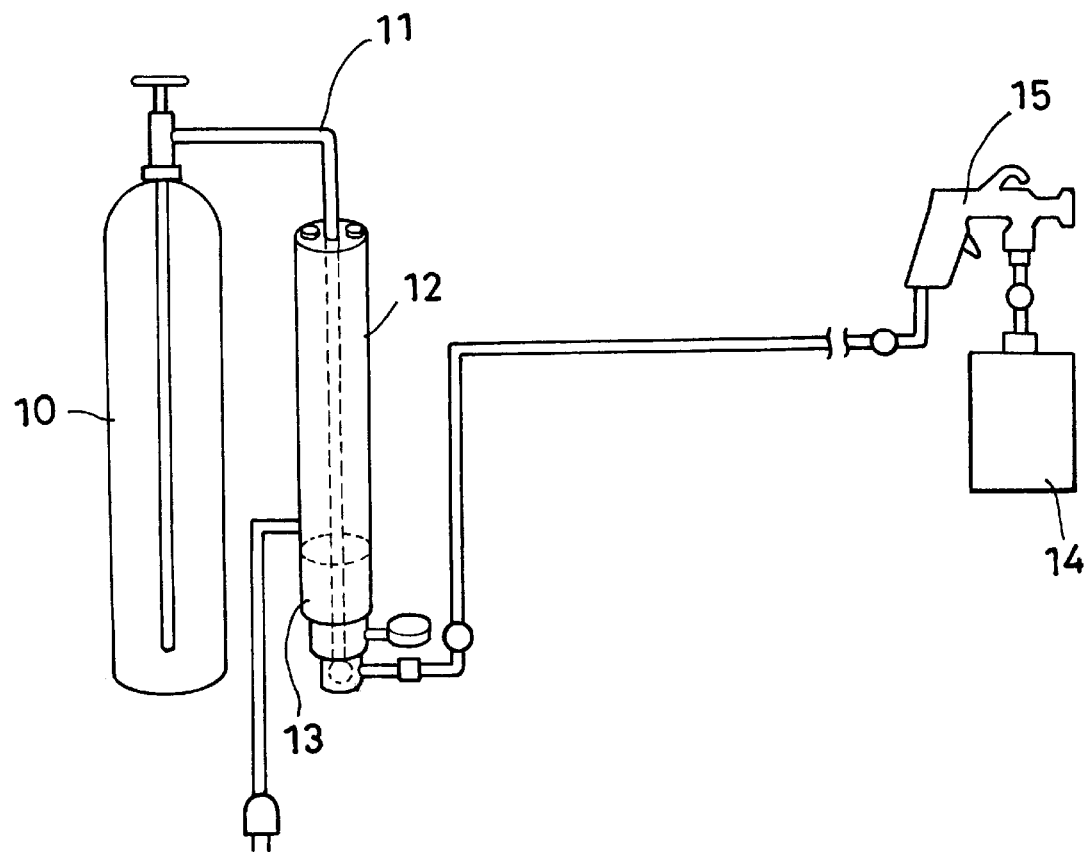

United States Patent [19]
Nakamura

[11] Patent Number: 6,043,287
[45] Date of Patent: *Mar. 28, 2000

[54] DISINFECTANT COMPOSITION AND A DISINFECTION METHOD USING THE SAME

[76] Inventor: Junsuke Nakamura, 74, Suimoncho, Nara-city, Nara, Japan

[*] Notice: This patent issued on a continued prosecution application filed under 37 CFR 1.53(d), and is subject to the twenty year patent term provisions of 35 U.S.C. 154(a)(2).

[21] Appl. No.: 08/611,836

[22] Filed: Mar. 6, 1996

Related U.S. Application Data

[63] Continuation of application No. 08/212,328, Mar. 14, 1994, abandoned, which is a continuation of application No. 07/936,055, Aug. 26, 1992, abandoned, which is a continuation of application No. 07/533,990, Jun. 6, 1990, abandoned.

[30] Foreign Application Priority Data

Jun. 23, 1989 [JP] Japan ..................................... 1-161270
Nov. 1, 1989 [JP] Japan ..................................... 1-286478

[51] Int. Cl.$^7$ ............................. A01N 33/18; A01N 35/00
[52] U.S. Cl. ........................................... 514/704; 514/705
[58] Field of Search ..................................... 514/704, 705

[56] References Cited

U.S. PATENT DOCUMENTS

| | | | |
|---|---|---|---|
| 3,912,809 | 10/1975 | Rendon | ..................................... 424/75 |
| 3,917,850 | 11/1975 | Boucher | ................................... 424/333 |
| 4,048,336 | 9/1977 | Winicov et al. | ........................ 424/334 |

OTHER PUBLICATIONS

Ellis et al 87CA: 1067605 1977.
Merck Index 7$^{th}$ Ed.

*Primary Examiner*—Russell Travers
*Attorney, Agent, or Firm*—Jordan and Hamburg LLP

[57] ABSTRACT

This invention provides a disinfectant composition which is suited to the disinfection of confined spaces such as the interior of an ambulance or the like. It is prepared extemporaneously by blending a highly concentrated alcohol with glutaraldehyde and a buffer solution such as an aqueous solution of diethanolamine. This composition containing 65 to 80% of alcohol and 2 to 4% of glutaraldehyde exhibits a strong and lasting disinfectant effect. The invention further provides a method for space disinfection which comprises atomizing and spraying this disinfectant composition by means of a high-pressure gas such as pressurized carbon dioxide gas.

16 Claims, 2 Drawing Sheets

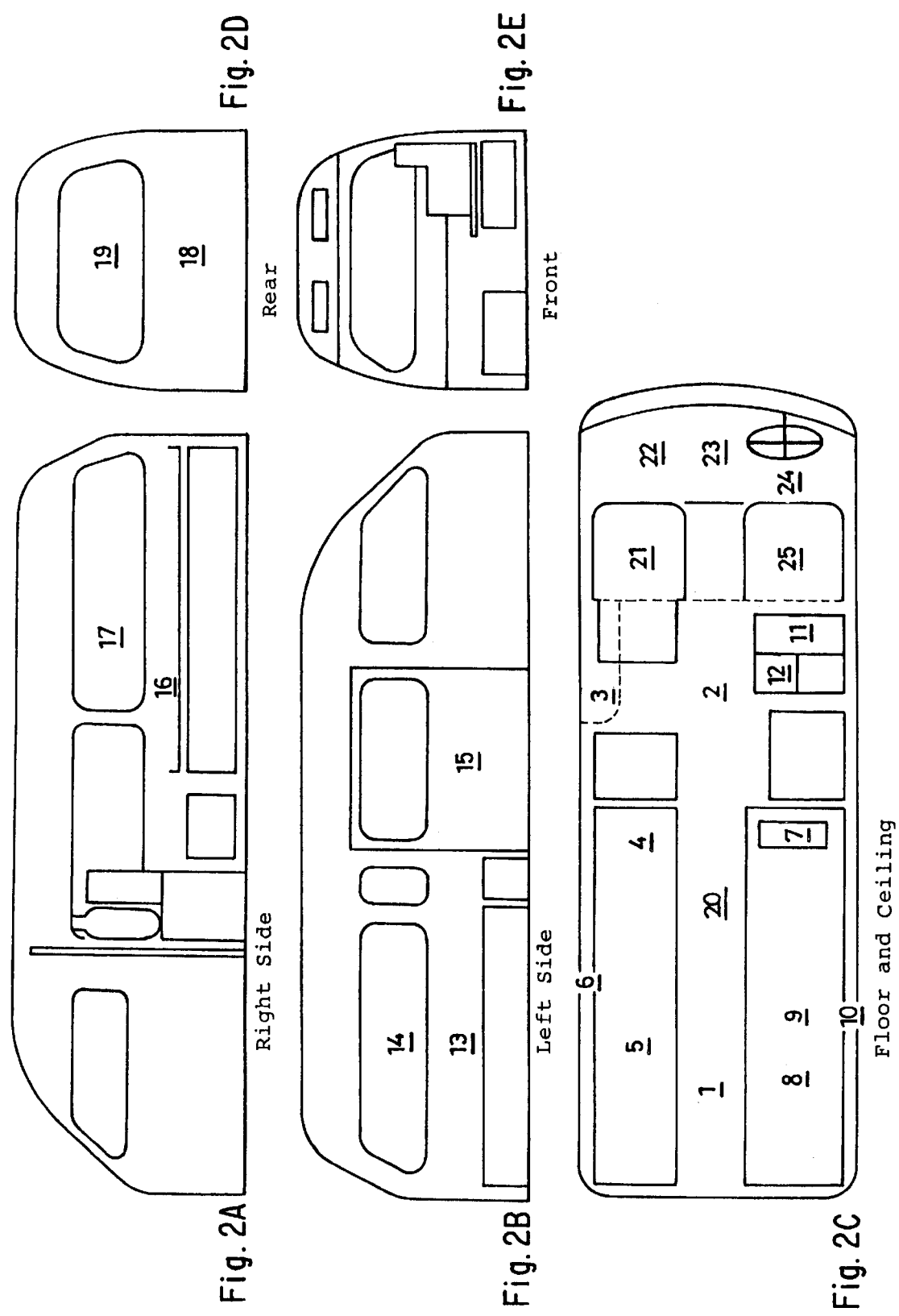

DISINFECTANT COMPOSITION AND A DISINFECTION METHOD USING THE SAME

This application is a continuation of application Ser. No. 08/212,328 filed Mar. 14, 1994, now abandoned, which is a continuation of application Ser. No. 07/936,055 filed Aug. 26, 1992, now abandoned, which is a continuation of application Ser. No. 07/533,990 filed Jun. 6, 1990, now abandoned.

BACKGROUND ART

1. Technical Field

The present invention relates to a disinfectant composition which can be used advantageously in the disinfection of generally confined areas, for example within buildings and vehicles such as buses, ambulances, etc., and to a disinfection method using said composition.

2. Background Art

In the disinfection of a confined area such as the interior of an ambulance, routine general cleaning must be followed by a time-consuming disinfection work which includes wiping with a swab and disinfectant solution.

The ambulance, for instance, must be maintained at least at a certain level of cleanliness because its function is to transport patients while they are given initial treatment, and for this purpose, routine disinfection is an important procedure. It is generally acknowledged that the mean viable count of coliform bacteria, staphylococci, general bacteria, fungi and so on should not be more than 10 colony-forming units (CFU/10 $cm^2$) and preferably not more than 5 CFU/10 $cm^2$ [Kyukyu Iryo no Kiso to Jissai: 1 Kyukyu Gyomu to Kyukyu Iryo] (The Fundamentals and Practice of Emergency Medicine: 1 Emergency Management and Emergency Medicine, edited by the Emergency Department of the Metropolitan Fire Board of Tokyo, published by Joho Kaihatsu Kenkyusho).

The conventional disinfection procedure comprises using an aqueous dilution of a certain disinfectant such as cresol by manual swab cleaning or spray cleaning with the aid of a hand-operated or electrically-driven sprayer. In some extraordinary or unavoidable cases, a disinfectant solution based on glutaraldehyde, which is known to be an effective sterilant/disinfectant, has been employed. Thus, for example, glutaral is diluted with water to a concentration of about 1 to 2 percent and applied by swab cleaning.

However, the conventional disinfection procedure is not only time-consuming but also inadequate in that all nooks and corners can hardly be reached for thorough disinfection. Moreover, as the diluted disinfectant solution is applied by spraying, the water remains on the treated surface and the desired disinfecting effect is not obtained in corner areas so that no satisfactory result is accomplished.

In addition, when said glutaraldehyde is used for swab cleaning, the irritating and pungent odor persists for a long time. Thus, the odor is in the air for as long as 12 to 24 hours.

It is an object of the present invention to provide a disinfectant composition which can be used advantageously in the disinfection of confined areas such as within the ambulance under all circumstances, is capable of providing a very high disinfecting effect, can be easily prepared in the field, and does not give off an irritating odor.

It is another object of the invention to provide a disinfection method by which said disinfectant composition can be applied uniformly to all the nooks and corners of such confined spaces.

SUMMARY OF THE INVENTION

The disinfectant composition provided by the present invention for solving the above-mentioned problems is characterized in that it is extemporaneously prepared by blending a highly concentrated alcohol with glutaraldehyde and a buffer solution such as an aqueous solution of diethanolamine to provide a composition containing 65 to 80% of alcohol and 2 to 4% of glutaraldehyde.

Preferably, the above composition is prepared by blending a basal mixture of said highly concentrated alcohol and a perfume with 10 to 20 volume percent of a 20% (aqueous) solution of glutaraldehyde and 3 to 7 volume percent of a buffer solution such as a 1.0 to 2.0% aqueous solution of diethanolamine.

Thus, since glutaraldehyde has an irritating odor which requires forced ventilation with a fan blower or the like following each cleaning job, a perfume is preferably added as mentioned above for masking this unpleasant odor.

Moreover, if the concentration of glutaraldehyde used in this blending is less than 2%, the disinfectant effect is markedly compromised, while the use of glutaraldehyde over the concentration of 4% is undesirable, for it then gives off an intense irritating odor during cleaning and causes a prolonged carryover of the odor after cleaning.

The concentration of alcohol in the disinfectant composition is preferably in the above-mentioned range of 65 to 80 percent, for both an excess and a shortage of alcohol result in a poor disinfectant effect.

The highly concentrated alcohol mentioned above may be a relatively volatile and biocidally active concentrated alcohol such as ethanol, methanol or of at least 80% concentration isopropyl alcohol, or the corresponding alcohol denatured with some denaturants. For example, there may be mentioned the denatured alcohols obtainable by blending highly concentrated ethanol with denaturants such as methanol, isopropyl alcohol, etc. or, more specifically the so-called methanol-denatured alcohol prepared by adding 5 kg of 95% methanol to each 200 l of 95% ethanol.

Since the use of ethanol alone is costly, it is preferable to use a denatured alcohol such as the above-mentioned methanol-denatured alcohol. Isopropyl alcohol of 80 to 90 percent concentration can also be used with advantage from the standpoint of safety.

With the above disinfectant composition, excellent sterilizing and disinfecting effects can be obtained by virtue of the disinfectant glutaraldehyde. Thus, glutaraldehyde is a chemically synthesized substance and has been shown to kill various bacteria, tubercle bacilli, fungi, bacterial spores, and viruses. The use of a solution of this glutaraldehyde diluted with alcohol produces a sufficient sterilizing and disinfecting effect.

Particularly because said basal concentrated alcohol is used as a diluent for glutaraldehyde, the glutaraldehyde can be well diluted and, in addition, the concentrated alcohol itself exerts an excellent sterilizing and disinfecting effect so that a sufficient effect can be obtained even with a moderate amount of glutaraldehyde.

Furthermore, as a buffer solution is included in the disinfectant composition, the pH of the application solution can be maintained at about 7.5 to 8.5 so that the disinfectant effect may last for about 10 days after application. Furthermore, the incorporation of the perfume as a masking agent is useful in cancelling the irritating odor of glutaraldehyde.

Moreover, since the disinfectant composition of the invention can be easily provided by blending said base alcohol, such as concentrated ethanol, isopropyl alcohol or a denatured alcohol prepared by using a methanol or the like as a denaturant, which may be optionally perfumed as mentioned above, with a commercial 20% solution of glutaraldehyde and a buffer solution such as an aqueous solution of diethanolamine, it can be easily prepared in the field and applied as it is.

The disinfection method using the above-mentioned disinfectant composition in accordance with the present invention is characterized in that a disinfectant composition prepared by the above blending procedure is comminuted and sprayed in finely divided form with the aid of a pressurized gas. Generally the above disinfectant composition is applied by spraying about 70 to 80 ml per 25 $m^3$.

With regard to the pressurized gas mentioned above, it is preferable to utilize the pressure of vaporization of liquefied carbon dioxide gas. In this case, the disinfectant composition must be sprayed in a mixing ratio well below the dust explosion limit of the alcohol with respect to carbon dioxide gas. The mixing ratio is, namely, about 0.001 volume part (%) of the disinfectant composition to 100 volume parts of carbon dioxide gas. Thus, the above ratio is recommended in view of the fact that the lower explosion limit of alcohol in the air is 3.3 volume percent.

The liquefied carbon dioxide gas is sprayed at a gauge pressure of about 3–6 $kg/cm^2$.

When sprayed in this manner, the above-mentioned disinfectant composition is atomized in the form of ultramicro particles and can diffuse uniformly into all the nooks and corners throughout the space sprayed therewith. The disinfectant effect of glutaraldehyde can be produced promptly.

Particularly when carbon dioxide gas is used, there is no possibility of chemical reactions with the active ingredient mentioned above, hence there is no fear of changes in properties of the composition, and the glutaraldehyde and highly concentrated alcohol in the disinfectant composition produce an excellent synergistic disinfectant effect.

Furthermore, when carbon dioxide gas is used as a high-pressure gas, the precipitation of disinfectant particles sprayed into the air can be promoted through the specific gravity effect of carbon dioxide gas. Moreover, the use of a large quantity of carbon dioxide gas can fully eliminate the possibility of ignition or explosion in spite of the use of alcohol as the base of the composition. Thus the composition can be sprayed safely even in places where there is heat of fire.

Therefore, said composition can be used to disinfect confined areas such as the interior of an ambulance car efficiently and reliably within a short period of time.

BRIEF DESCRIPTION OF THE DRAWINGS

FIG. 1 is a schematic front view of a sprayer which utilizes liquefied carbon dioxide and is to be used for disinfection in the practice of the present invention.

FIGS. 2A, 2B, 2C, 2D and 2E shows an ambulance in developments to indicate the points for checking for microorganisms.

DETAILED DESCRIPTION OF PREFERRED EMBODIMENTS

Example 1

A disinfectant composition containing ethanol (alcohol) in a concentration of 71.25% and glutaraldehyde in a concentration of 4.00% was prepared by blending 850 ml of 95% ethanol, 200 ml of a 20% aqueous solution of glutaraldehyde (Maruishi Pharmaceutical's STERIHYDE L) and 50 ml of a buffer solution, namely a 1.25% aqueous solution of diethanolamine as prepared by dissolving 1.25 ml of 99% diethanolamine in 98.75 ml of distilled water.

This disinfectant composition could remain at pH 8.0 even after the lapse of 10 days without any chemical changes of the active ingredient.

This disinfectant composition was applied to two ambulances (ambulance A in service and spare ambulance B) by spraying 40 ml of the composition into each ambulance (12.67 $m^3$ in space volume) through four sites, namely the right and left doors relative to the driver's seat, one side slide door and the rear swing-up door over 40 seconds by means of a sprayer utilizing the pressure of vaporization of liquefied carbon dioxide gas. Then the ambulance were tightly closed for 20 minutes for effecting disinfection.

The sprayer mentioned above has, as shown in FIG. 1, for instance, a heater (12) whose temperature is controllable and a pressure adjuster (13) in the discharge line (11) from a carbon dioxide cylinder (10) filled with carbon dioxide gas and equipped with a siphon type delivery mechanism, with a disinfectant composition tank (14) and said discharge line (11) each being connected to a spray gun (15). The liquefied carbon dioxide is warmed for evaporation and then delivery and, at the same time, the pressure of said vaporized gas is utilized to spray the disinfectant composition supplied in the tank (14).

After the above disinfection treatment, four classes of microorganisms, namely coliform bacteria, staphylococci, general bacteria and fungi, were searched for at various source points given underlined numbers 1 to 25 in FIGS. 2A, 2B, 2C, 2D and 2E. For the detection of the four groups of microorganisms, the colonies formed on cultivation with the respective specified media were counted. The results thus obtained are shown below in Table 1.

For comparison with the data obtained after the disinfection treatment, the results of the same microorganism counting (before treatment) carried out immediately after car inside cleaning (wiping with wet cloth) are also shown.

Example 2

Synthetic methanol-denatured alcohol prepared by adding 24 ml of 95% methanol to 766.0 ml of 95% ethanol was used as the diluent alcohol, and a mixture of 790 ml of said diluent alcohol and 10 ml of a perfume for masking was used as a base. A disinfectant composition having an alcohol concentration of about 76% and a glutaraldehyde concentration of 3% was prepared by blending said base, 150 ml of the same 20% aqueous solution of glutaraldehyde as used in Example 1 (same STERIHYDE L as mentioned above) and 50 ml of a buffer solution, namely a 1% aqueous solution of diethanolamine as prepared by dissolving 1 ml of 99% diethanolamine in 99 ml of distilled water. This disinfectant composition could remain at pH 7.8 to 8.2 even after the lapse of 10 days without any chemical changes of the active ingredient.

This disinfectant composition was applied to two ambulances (ambulance A in service and spare ambulance B) in the same manner as in Example 1 by spraying 40 ml of the composition into each ambulance (12.67 $m^3$ in space volume) through three sites, namely two left door sites and the rear swing-up door over 40 seconds, by means of a sprayer utilizing the pressure of vaporization of liquefied carbon dioxide. The ambulances were then hermetically closed for 20 minutes for achieving the disinfection.

Then, the four classes of microorganisms were searched for at the same 25 points as mentioned above. For comparison, the same microorganism counting was performed before the disinfection treatment. The results thus obtained are shown below in Table 2 in the same manner as in Example 1.

Example 3

In this example, use was made of 88.7% isopropyl alcohol as the diluent alcohol in lieu of the synthetic methanol-denatured alcohol used above in Example 2. A mixture of 780 ml of said alcohol and 20 ml of a perfume for masking was used as a base. A disinfectant composition having an alcohol concentration of about 70% and a glutaraldehyde concentration of 3% was prepared by blending said base, 150 ml of a 20% glutaraldehyde solution (same STERIHYDE L as mentioned above) and 50 ml of a buffer solution, namely a 2% aqueous solution of diethanolamine (prepared by dissolving 2 ml of 99% diethanolamine in 98 ml of distilled water).

Like the disinfectant composition of Example 2, this disinfectant composition, too, could remain at pH 7.8 or above even after the lapse of 10 days without any chemical changes of the active ingredient.

This disinfectant composition was used for ambulance disinfection by spraying it in the same manner as in Example 2, followed by checking for microorganisms. Almost the same results were obtained as those obtained with the disinfectant composition of Example 2.

Comparative Example

For comparison, a disinfectant composition was prepared by blending a mixture of 760 ml of 95% ethanol and 200.0 ml of a 20% chlorhexidine gluconate solution (Maruishi Pharmaceuticals's 20% MASKIN solution), 40.0 ml of a 20% glutaraldehyde solution (same STERIHYDE L as mentioned above) and 0.8 ml of 99% diethanolamine (buffer). This disinfectant composition had a pH of 8.0 as measured immediately after preparation thereof. After the lapse of 4 hours, however, the composition became turbid due to the reaction between the MASKIN solution and diethanolamine and showed a pH of 7.2.

The disinfectant composition of this comparative example was applied to the same two ambulances (ambulance A in service and spare ambulance B) as used in the foregoing examples by spraying 20 ml of the composition into each car (estimatingly 9 $m^3$ in space volume) through two sites, namely the door left to the driver's seat and the rear swing-up door, over 20 seconds by means of a sprayer utilizing the pressure of vaporization of liquefied carbon dioxide. The cars were then tightly closed for 15 minutes for effecting disinfection, followed by checking for microorganisms at the same 25 points as mentioned above. The same checking for microorganisms was performed also before treatment. The results thus obtained are shown below in Table 3.

TABLE 1

Microbial Count: colony forming units (CFU/10 $cm^2$)

| | | Ambulance car A (car on service) | | | | | | | |
|---|---|---|---|---|---|---|---|---|---|
| | | General bacteria | | Coliform bacteria | | Staphylococci | | Fungi | |
| | Source | Before treatment | After treatment | Before treatment | After treatment | Before treatment | After treatment | Before treatment | After treatment |
| 1 | Center of rear floor | 100 | 0 | 0 | 0 | 0 | 0 | 6 | 0 |
| 2 | Center of floor adjacent to side door | 100 | 3 | 0 | 0 | 7 | 0 | 10 | 2 |
| 3 | Step at side door | 100 | 2 | 0 | 0 | 17 | 0 | 31 | 3 |
| 4 | Surface of side seat | 100 | 0 | 0 | 0 | 0 | 0 | 0 | 0 |
| 5 | Lid of underside compartment | 100 | 1 | 0 | 0 | 0 | 0 | 0 | 0 |
| 6 | Floor of underside compartment | 100 | 0 | 0 | 0 | 11 | 0 | 5 | 0 |
| 7 | Underside of patient's pillow | 10 | 0 | 0 | 0 | 2 | 0 | 6 | 0 |
| 8 | Surface of stretcher | 0 | 0 | 0 | 0 | 0 | 0 | 5 | 1 |
| 9 | Surface of wheel stretcher | 9 | 0 | 0 | 0 | 15 | 0 | 17 | 2 |
| 10 | Floor under wheel stretcher | 0 | 0 | 4 | 0 | 0 | 0 | 0 | 0 |
| 11 | Surface of oxygen bomb | 4 | 0 | 0 | 0 | 0 | 0 | 0 | 0 |
| 12 | Surface of wash basin | 0 | 0 | 0 | 0 | 0 | 0 | 0 | 0 |
| 13 | Center of left side wall | 0 | 0 | 0 | 0 | 0 | 0 | 2 | 1 |
| 14 | Center of left window glass | 0 | 0 | 0 | 0 | 0 | 0 | 0 | 0 |
| 15 | Inner side of side door | 2 | 0 | 0 | 0 | 0 | 0 | 1 | 0 |
| 16 | Center of right side wall | 0 | 0 | 0 | 0 | 0 | 0 | 2 | 0 |
| 17 | Center of right window glass | 0 | 0 | 0 | 0 | 0 | 0 | 0 | 0 |
| 18 | Center of inner surface of rear door | 0 | 0 | 0 | 0 | 0 | 0 | 0 | 0 |

TABLE 1-continued

Microbial Count: colony forming units (CFU/10 cm$^2$)

| | | | | | | | | | |
|---|---|---|---|---|---|---|---|---|---|
| 19 | Center of rear window glass | 0 | 0 | 0 | 0 | 0 | 0 | 0 | 0 |
| 20 | Center of ceiling | 0 | 0 | 0 | 0 | 0 | 0 | 0 | 0 |
| 21 | Helper's seat | 4 | 1 | 0 | 0 | 0 | 0 | 5 | 2 |
| 22 | Telephone set at driver's seat | 10 | 0 | 0 | 0 | 0 | 0 | 0 | 0 |
| 23 | Dashboard before helper's seat | 100 | 3 | 0 | 0 | 14 | 0 | 4 | 1 |
| 24 | Steering wheel | 0 | 0 | 0 | 0 | 2 | 0 | 0 | 0 |
| 25 | Driver's seat | 14 | 1 | 0 | 0 | 0 | 0 | 0 | 0 |
| Total | | 753 | 11 | 4 | 0 | 68 | 0 | 94 | 12 |
| Mean | | 30.12 | 0.44 | 0.16 | 0 | 2.72 | 0 | 3.76 | 0.48 |
| SD | (standard deviation) | 43.74 | 0.90 | 0.78 | 0 | 5.30 | 0 | 6.84 | 0.85 |
| SE | (standard error) | 8.75 | 0.18 | 0.16 | 0 | 1.06 | 0 | 1.37 | 0.17 |
| AR | (appearance rate %) | 56 | 24 | 4 | 0 | 28 | 0 | 48 | 28 |

| | | Ambulance car B (spare car) | | | | | | | |
|---|---|---|---|---|---|---|---|---|---|
| | | General bacteria | | Coliform bacteria | | Staphylococci | | Fungi | |
| | Source | Before treatment | After treatment | Before treatment | After treatment | Before treatment | After treatment | Before treatment | After treatment |
| 1 | Center of rear floor | 0 | 0 | 0 | 0 | 0 | 0 | 8 | 2 |
| 2 | Center of floor adjacent to side door | 0 | 0 | 0 | 0 | 0 | 0 | 11 | 3 |
| 3 | Step at side door | 0 | 0 | 0 | 0 | 18 | 0 | 15 | 1 |
| 4 | Surface of side seat | 0 | 0 | 0 | 0 | 0 | 0 | 0 | 0 |
| 5 | Lid of underside compartment | 0 | 0 | 0 | 0 | 0 | 0 | 0 | 1 |
| 6 | Floor of underside compartment | 0 | 0 | 0 | 0 | 0 | 0 | 2 | 1 |
| 7 | Underside of patient's pillow | 2 | 0 | 0 | 0 | 0 | 0 | 1 | 1 |
| 8 | Surface of stretcher | 0 | 0 | 0 | 0 | 0 | 0 | 11 | 0 |
| 9 | Surface of wheel stretcher | 0 | 0 | 0 | 0 | 0 | 0 | 4 | 0 |
| 10 | Floor under wheel stretcher | 0 | 0 | 0 | 0 | 0 | 0 | 0 | 0 |
| 11 | Surface of oxygen bomb | 100 | 4 | 0 | 0 | 0 | 0 | 0 | 0 |
| 12 | Surface of wash basin | 0 | 0 | 0 | 0 | 6 | 0 | 4 | 1 |
| 13 | Center of left side wall | 0 | 0 | 0 | 0 | 0 | 0 | 0 | 0 |
| 14 | Center of left window glass | 0 | 0 | 0 | 0 | 0 | 0 | 0 | 0 |
| 15 | Inner side of side door | 0 | 0 | 0 | 0 | 0 | 0 | 0 | 0 |
| 16 | Center of right side wall | 0 | 0 | 0 | 0 | 0 | 0 | 0 | 0 |
| 17 | Center of right window glass | 0 | 0 | 0 | 0 | 0 | 0 | 0 | 0 |
| 18 | Center of inner surface of rear door | 0 | 0 | 0 | 0 | 0 | 0 | 3 | 0 |
| 19 | Center of rear window glass | 0 | 0 | 0 | 0 | 0 | 0 | 0 | 0 |
| 20 | Center of ceiling | 0 | 0 | 0 | 0 | 0 | 0 | 0 | 0 |
| 21 | Helper's seat | 100 | 3 | 0 | 0 | 0 | 0 | 1 | 1 |
| 22 | Telephone set at driver's seat | 0 | 0 | 0 | 0 | 0 | 0 | 0 | 0 |
| 23 | Dashboard before helper's seat | 0 | 1 | 0 | 0 | 0 | 0 | 3 | 0 |
| 24 | Steering wheel | 0 | 0 | 0 | 0 | 0 | 0 | 0 | 0 |
| 25 | Driver's seat | 0 | 1 | 0 | 0 | 0 | 0 | 7 | 1 |
| Total | | 202 | 9 | 0 | 0 | 24 | 0 | 70 | 12 |
| Mean | | 8.08 | 0.36 | 0 | 0 | 0.96 | 0 | 2.80 | 0.48 |
| SD | (standard deviation) | 27.02 | 0.98 | 0 | 0 | 3.67 | 0 | 4.20 | 0.76 |
| SE | (standard error) | 5.42 | 0.20 | 0 | 0 | 0.73 | 0 | 0.84 | 0.15 |
| AR | (appearance rate %) | 12 | 16 | 0 | 0 | 8 | 0 | 48 | 32 |

TABLE 2

Microbial Count: colony forming units (CFU/10 cm$^2$)

Ambulance car A (car on service)

| | Source | General bacteria Before treatment | General bacteria After treatment | Coliform bacteria Before treatment | Coliform bacteria After treatment | Staphylococci Before treatment | Staphylococci After treatment | Fungi Before treatment | Fungi After treatment |
|---|---|---|---|---|---|---|---|---|---|
| 1 | Center of rear floor | 31 | 3 | 0 | 0 | 63 | 0 | 7 | 4 |
| 2 | Center of floor adjacent to side door | 100 | 2 | 0 | 0 | 100 | 0 | 11 | 1 |
| 3 | Step at side door | 100 | 6 | 3 | 0 | 100 | 0 | 12 | 0 |
| 4 | Surface of side seat | 100 | 3 | 0 | 0 | 1 | 0 | 5 | 1 |
| 5 | Lid of underside compartment | 12 | 1 | 0 | 0 | 0 | 0 | 11 | 2 |
| 6 | Floor of underside compartment | 100 | 2 | 0 | 0 | 16 | 0 | 5 | 1 |
| 7 | Underside of patient's pillow | 1 | 2 | 0 | 0 | 2 | 0 | 6 | 2 |
| 8 | Surface of stretcher | 26 | 0 | 0 | 0 | 0 | 0 | 2 | 1 |
| 9 | Surface of wheel stretcher | 22 | 2 | 0 | 0 | 0 | 0 | 0 | 0 |
| 10 | Floor under wheel stretcher | 100 | 8 | 0 | 0 | 19 | 0 | 21 | 2 |
| 11 | Surface of oxygen bomb | 2 | 1 | 0 | 0 | 0 | 0 | 0 | 0 |
| 12 | Surface of wash basin | 0 | 0 | 0 | 0 | 0 | 0 | 16 | 1 |
| 13 | Center of left side wall | 7 | 1 | 0 | 0 | 0 | 0 | 0 | 0 |
| 14 | Center of left window glass | 0 | 0 | 0 | 0 | 0 | 0 | 0 | 0 |
| 15 | Inner side of side door | 3 | 0 | 0 | 0 | 2 | 0 | 1 | 1 |
| 16 | Center of right side wall | 100 | 0 | 0 | 0 | 0 | 0 | 4 | 0 |
| 17 | Center of right window glass | 2 | 0 | 0 | 0 | 0 | 0 | 0 | 0 |
| 18 | Center of inner surface of rear door | 0 | 0 | 0 | 0 | 0 | 0 | 0 | 0 |
| 19 | Center of rear window glass | 0 | 0 | 0 | 0 | 0 | 0 | 0 | 0 |
| 20 | Center of ceiling | 0 | 0 | 0 | 0 | 0 | 0 | 0 | 0 |
| 21 | Helper's seat | 8 | 1 | 0 | 0 | 0 | 0 | 0 | 0 |
| 22 | Telephone set at driver's seat | 3 | 0 | 0 | 0 | 0 | 0 | 2 | 1 |
| 23 | Dashboard before helper's seat | 0 | 0 | 0 | 0 | 0 | 0 | 1 | 0 |
| 24 | Steering wheel | 0 | 0 | 0 | 0 | 0 | 0 | 6 | 2 |
| 25 | Driver's seat | 100 | 1 | 0 | 0 | 0 | 0 | 8 | 1 |
| Total | | 817 | 33 | 3 | 0 | 303 | 0 | 118 | 20 |
| Mean | | 32.68 | 1.32 | 0.12 | 0 | 12.12 | 0 | 4.72 | 0.80 |
| SD | (standard deviation) | 42.77 | 1.95 | 0.59 | 0 | 28.93 | 0 | 7.38 | 0.98 |
| SE | (standard error) | 8.55 | 0.39 | 0.12 | 0 | 5.79 | 0 | 1.48 | 0.20 |
| AR | (appearance rate %) | 68 | 52 | 4 | 0 | 32 | 0 | 64 | 52 |

Ambulance car B (spare car)

| | Source | General bacteria Before treatment | General bacteria After treatment | Coliform bacteria Before treatment | Coliform bacteria After treatment | Staphylococci Before treatment | Staphylococci After treatment | Fungi Before treatment | Fungi After treatment |
|---|---|---|---|---|---|---|---|---|---|
| 1 | Center of rear floor | 100 | 7 | 0 | 0 | 72 | 0 | 17 | 0 |
| 2 | Center of floor adjacent to side door | 100 | 7 | 0 | 0 | 100 | 0 | 17 | 0 |
| 3 | Step at side door | 100 | 14 | 4 | 0 | 100 | 0 | 9 | 2 |
| 4 | Surface of side seat | 2 | 1 | 0 | 0 | 0 | 0 | 0 | 0 |
| 5 | Lid of underside compartment | 4 | 0 | 0 | 0 | 0 | 0 | 0 | 0 |
| 6 | Floor of underside compartment | 100 | 12 | 2 | 0 | 42 | 0 | 22 | 2 |
| 7 | Underside of patient's pillow | 18 | 1 | 0 | 0 | 0 | 0 | 74 | 0 |
| 8 | Surface of stretcher | 100 | 7 | 0 | 0 | 16 | 0 | 56 | 4 |

TABLE 2-continued

Microbial Count: colony forming units (CFU/10 cm$^2$)

| | | | | | | | | | |
|---|---|---|---|---|---|---|---|---|---|
| 9 | Surface of wheel stretcher | 100 | 4 | 0 | 0 | 4 | 0 | 6 | 4 |
| 10 | Floor under wheel stretcher | 100 | 10 | 0 | 0 | 10 | 0 | 12 | 1 |
| 11 | Surface of oxygen bomb | 47 | 0 | 0 | 0 | 0 | 0 | 0 | 2 |
| 12 | Surface of wash basin | 21 | 1 | 0 | 0 | 0 | 0 | 5 | 0 |
| 13 | Center of left side wall | 0 | 0 | 0 | 0 | 0 | 0 | 0 | 0 |
| 14 | Center of left window glass | 0 | 0 | 0 | 0 | 0 | 0 | 0 | 0 |
| 15 | Inner side of side door | 2 | 0 | 0 | 0 | 0 | 0 | 0 | 0 |
| 16 | Center of right side wall | 12 | 0 | 0 | 0 | 0 | 0 | 0 | 0 |
| 17 | Center of right window glass | 100 | 0 | 0 | 0 | 34 | 0 | 19 | 0 |
| 18 | Center of inner surface of rear door | 0 | 0 | 0 | 0 | 0 | 0 | 0 | 0 |
| 19 | Center of rear window glass | 0 | 0 | 0 | 0 | 0 | 0 | 0 | 0 |
| 20 | Center of ceiling | 0 | 0 | 0 | 0 | 0 | 0 | 0 | 0 |
| 21 | Helper's seat | 22 | 0 | 0 | 0 | 0 | 0 | 0 | 0 |
| 22 | Telephone set at driver's seat | 100 | 0 | 0 | 0 | 0 | 0 | 0 | 0 |
| 23 | Dashboard before helper's seat | 100 | 1 | 0 | 0 | 3 | 0 | 11 | 2 |
| 24 | Steering wheel | 1 | 0 | 0 | 0 | 0 | 0 | 0 | 0 |
| 25 | Driver's seat | 100 | 0 | 0 | 0 | 7 | 0 | 0 | 0 |
| Total | | 1229 | 65 | 6 | 0 | 388 | 0 | 248 | 17 |
| Mean | | 49.16 | 2.60 | 0.24 | 0 | 15.52 | 0 | 9.92 | 0.68 |
| SD | (standard deviation) | 46.13 | 4.19 | 0.86 | 0 | 30.01 | 0 | 17.87 | 1.22 |
| SE | (standard error) | 9.23 | 0.84 | 0.17 | 0 | 6.00 | 0 | 3.57 | 0.25 |
| AR | (appearance rate %) | 80 | 44 | 8 | 0 | 40 | 0 | 44 | 28 |

TABLE 3

Microbial Count: colony forming units (CFU/10 cm$^2$)

Ambulance car A (car on service)

| | Source | General bacteria | | Coliform bacteria | | Staphylococci | | Fungi | |
|---|---|---|---|---|---|---|---|---|---|
| | | Before treatment | After treatment | Before treatment | After treatment | Before treatment | After treatment | Before treatment | After treatment |
| 1 | Center of rear floor | 37 | 2 | 0 | 0 | 12 | 0 | 12 | 2 |
| 2 | Center of floor adjacent to side door | 45 | 9 | 0 | 0 | 16 | 6 | 11 | 7 |
| 3 | Step at side door | 100 | 11 | 44 | 2 | 61 | 5 | 36 | 8 |
| 4 | Surface of side seat | 4 | 0 | 0 | 0 | 5 | 1 | 3 | 0 |
| 5 | Lid of underside compartment | 13 | 0 | 0 | 0 | 0 | 0 | 0 | 0 |
| 6 | Floor of underside compartment | 16 | 0 | 0 | 0 | 0 | 0 | 10 | 0 |
| 7 | Underside of patient's pillow | 100 | 0 | 0 | 0 | 0 | 0 | 0 | 0 |
| 8 | Surface of stretcher | 100 | 0 | 2 | 0 | 0 | 0 | 4 | 0 |
| 9 | Surface of wheel stretcher | 8 | 0 | 0 | 0 | 2 | 0 | 0 | 0 |
| 10 | Floor under wheel stretcher | 17 | 0 | 0 | 0 | 0 | 0 | 2 | 1 |
| 11 | Surface of oxygen bomb | 11 | 1 | 0 | 0 | 0 | 0 | 0 | 0 |
| 12 | Surface of wash basin | 0 | 0 | 0 | 0 | 0 | 0 | 0 | 2 |
| 13 | Center of left side wall | 2 | 0 | 0 | 0 | 0 | 0 | 0 | 0 |
| 14 | Center of left window glass | 0 | 0 | 0 | 0 | 0 | 0 | 0 | 0 |
| 15 | Inner side of side door | 100 | 1 | 0 | 0 | 2 | 0 | 16 | 4 |

TABLE 3-continued

Microbial Count: colony forming units (CFU/10 cm$^2$)

| | | | | | | | | | |
|---|---|---|---|---|---|---|---|---|---|
| 16 | Center of right side wall | 0 | 0 | 0 | 0 | 0 | 0 | 0 | 0 |
| 17 | Center of right window glass | 0 | 0 | 0 | 0 | 0 | 0 | 0 | 0 |
| 18 | Center of inner surface of rear door | 11 | 0 | 0 | 0 | 0 | 0 | 0 | 1 |
| 19 | Center of rear window glass | 4 | 0 | 0 | 0 | 0 | 0 | 0 | 0 |
| 20 | Center of ceiling | 0 | 0 | 0 | 0 | 0 | 0 | 0 | 0 |
| 21 | Helper's seat | 6 | 0 | 0 | 0 | 0 | 0 | 3 | 0 |
| 22 | Telephone set at driver's seat | 4 | 0 | 0 | 0 | 0 | 0 | 1 | 0 |
| 23 | Dashboard before helper's seat | 6 | 0 | 0 | 0 | 4 | 0 | 3 | 0 |
| 24 | Steering wheel | 11 | 0 | 0 | 0 | 0 | 0 | 1 | 0 |
| 25 | Driver's seat | 6 | 0 | 0 | 0 | 5 | 0 | 0 | 0 |
| Total | | 601 | 24 | 46 | 2 | 107 | 12 | 102 | 25 |
| Mean | | 24.04 | 0.96 | 1.84 | 0.08 | 4.28 | 0.48 | 4.08 | 1.00 |
| SD | (standard deviation) | 34.78 | 2.72 | 8.62 | 0.39 | 12.22 | 1.50 | 7.87 | 2.14 |
| SE | (standard error) | 6.96 | 0.54 | 1.72 | 0.08 | 2.45 | 0.30 | 1.58 | 0.43 |
| AR | (appearance rate %) | 76 | 20 | 8 | 4 | 32 | 12 | 48 | 28 |

| | | Ambulance car B (spare car) | | | | | | | |
|---|---|---|---|---|---|---|---|---|---|
| | | General bacteria | | Coliform bacteria | | Staphylococci | | Fungi | |
| | Source | Before treatment | After treatment | Before treatment | After treatment | Before treatment | After treatment | Before treatment | After treatment |
| 1 | Center of rear floor | 100 | 3 | 0 | 0 | 26 | 2 | 14 | 4 |
| 2 | Center of floor adjacent to side door | 24 | 0 | 0 | 0 | 0 | 0 | 6 | 1 |
| 3 | Step at side door | 41 | 7 | 0 | 0 | 0 | 0 | 12 | 3 |
| 4 | Surface of side seat | 3 | 0 | 0 | 0 | 0 | 0 | 7 | 0 |
| 5 | Lid of underside compartment | 0 | 0 | 0 | 0 | 1 | 0 | 2 | 0 |
| 6 | Floor of underside compartment | 0 | 0 | 0 | 0 | 0 | 0 | 11 | 2 |
| 7 | Underside of patient's pillow | 2 | 0 | 0 | 0 | 0 | 0 | 21 | 0 |
| 8 | Surface of stretcher | 1 | 0 | 0 | 0 | 0 | 0 | 15 | 5 |
| 9 | Surface of wheel stretcher | 1 | 0 | 0 | 0 | 0 | 0 | 3 | 1 |
| 10 | Floor under wheel stretcher | 0 | 0 | 0 | 0 | 0 | 0 | 0 | 1 |
| 11 | Surface of oxygen bomb | 11 | 0 | 0 | 0 | 0 | 0 | 2 | 0 |
| 12 | Surface of wash basin | 5 | 0 | 0 | 0 | 0 | 0 | 12 | 2 |
| 13 | Center of left side wall | 0 | 0 | 0 | 0 | 0 | 0 | 0 | 0 |
| 14 | Center of left window glass | 4 | 1 | 0 | 0 | 0 | 0 | 0 | 0 |
| 15 | Inner side of side door | 0 | 0 | 0 | 0 | 0 | 0 | 0 | 0 |
| 16 | Center of right side wall | 0 | 0 | 0 | 0 | 0 | 0 | 4 | 0 |
| 17 | Center of right window glass | 0 | 0 | 0 | 0 | 0 | 0 | 0 | 0 |
| 18 | Center of inner surface of rear door | 0 | 0 | 0 | 0 | 0 | 0 | 0 | 0 |
| 19 | Center of rear window glass | 0 | 0 | 0 | 0 | 0 | 0 | 0 | 0 |
| 20 | Center of ceiling | 0 | 0 | 0 | 0 | 0 | 0 | 0 | 0 |
| 21 | Helper's seat | 8 | 0 | 0 | 0 | 0 | 0 | 0 | 0 |
| 22 | Telephone set at driver's seat | 25 | 0 | 0 | 0 | 0 | 0 | 11 | 2 |
| 23 | Dashboard before helper's seat | 4 | 0 | 0 | 0 | 7 | 0 | 4 | 0 |
| 24 | Steering wheel | 67 | 0 | 0 | 0 | 6 | 0 | 0 | 0 |
| 25 | Driver's seat | 10 | 0 | 0 | 0 | 0 | 0 | 3 | 0 |
| Total | | 306 | 11 | 0 | 0 | 40 | 2 | 127 | 21 |
| Mean | | 12.24 | 0.44 | 0 | 0 | 1.60 | 0.08 | 5.08 | 0.84 |
| SD | (standard deviation) | 23.65 | 1.47 | 0 | 0 | 5.28 | 0.39 | 5.97 | 1.38 |

TABLE 3-continued

| | | Microbial Count: colony forming units (CFU/10 cm$^2$) | | | | | | | |
|---|---|---|---|---|---|---|---|---|---|
| SE | (standard error) | 4.73 | 0.29 | 0 | 0 | 1.06 | 0.08 | 1.19 | 0.28 |
| AR | (appearance rate %) | 60 | 8 | 0 | 0 | 16 | 4 | 60 | 36 |

As indicated by the data given above in Tables 1 to 3, it was found that, as a result of the disinfection treatment in Example 1 as well as in Example 2, the numbers of microorganisms detected at the respective points and the mean number of microorganisms were very markedly reduced as compared with the corresponding data before treatment, the disinfectant effect being such that the values particularly desired in emergency medicine could be fully cleared.

Although the composition of Example 1 gives off an irritating odor characteristic of glutaraldehyde, the time required for the spraying treatment according to the invention is very short, so that forced ventilation by means of a fan following the disinfection treatment can eliminate the residual odor. Hence, the composition of Example 1 is also usable as a disinfectant.

In particular, the disinfectant compositions of Examples 2 and 3 contain a perfume for masking, so that they do not leave the irritating odor of glutaraldehyde and therefore are improved versions of the composition of Example 1 and particularly suited for use.

Although the disinfectant composition for comparison also produced a sufficient disinfectant effect, said composition allowed chemical reactions to occur. After the lapse of 4 hours, the pH became 7.2 and the disinfectant effect decreased in a relatively short period of time; the composition was thus inferior in stability.

As mentioned above, the disinfectant composition according to the invention, when sprayed utilizing the pressure of vaporization of liquefied carbon dioxide, produced a disinfectant effect which was comparable or superior to the effect obtainable by wiping or spraying with any of the conventional active ingredients. The spray treatment required only a short period of time and uniform disinfection treatment could be achieved in all the nooks and corners.

I claim:

1. A method of disinfection, comprising:

preparing and placing in a container a disinfectant composition including from about 65% to about 80% alcohol;

supplying a pressurized carbon dioxide propellant from a pressurized cylinder of liquified carbon dioxide to said disinfectant composition when spraying said disinfectant composition, said pressurized cylinder of liquified carbon dioxide being separate from said container of said disinfectant composition; and spraying said disinfectant composition using the pressurized carbon dioxide propellant supplied thereto at a mixing ratio below the dust explosion limit of the alcohol with respect to carbon dioxide gas.

2. The method according to claim 1, wherein said carbon dioxide propellant is supplied at a gauge pressure of from about 3 to about 6 kg/cm$^2$.

3. The method according to claim 1, wherein a mixing ratio in said step of spraying is about 0.001 volume parts of said disinfectant to 100 volume parts said carbon dioxide.

4. The method according to claim 3, wherein a balance of said disinfectant composition in said step of preparing includes glutaraldehyde added as a disinfectant, and a buffer solution to maintain a desired pH level.

5. The method according to claim 3, wherein said carbon dioxide propellant is supplied at a gauge pressure of from about 3 to about 6 kg/cm$^2$.

6. The method according to claim 3, wherein an amount of said disinfectant composition to be sprayed in said step of spraying is from about 70 ml to about 80 ml per 25 m$^3$ of a confined space.

7. The method according to claim 3, wherein:

a balance of said disinfectant composition in said step of preparing includes glutaraldehyde added as a disinfectant, and a buffer solution to maintain a desired pH level; and said buffer solution includes an aqueous solution of diethanolamine.

8. The method according to claim 7, wherein an amount of said disinfectant composition to be sprayed in said step of spraying is from about 70 ml to about 80 ml per 25 m$^3$ of a confined space.

9. The method according to claim 1, wherein a balance of said disinfectant composition in said step of preparing includes glutaraldehyde added as a disinfectant, and a buffer solution to maintain a desired pH level.

10. The method according to claim 9, wherein said buffer solution includes an aqueous solution of diethanolamine.

11. The method according to claim 1, wherein an amount of said disinfectant composition to be sprayed in said step of spraying is from about 70 ml to about 80 ml per 25 m$^3$ of a confined space.

12. The method according to claim 11, wherein said carbon dioxide propellant is supplied at a gauge pressure of from about 3 to about 6 kg/cm$^2$.

13. The method according to claim 11, wherein a mixing ratio in said step of spraying is about 0.001 volume parts of said disinfectant to 100 volume parts said carbon dioxide.

14. The method according to claim 13, wherein said carbon dioxide propellant is supplied at a gauge pressure of from about 3 to about 6 kg/cm$^2$.

15. The method according to claim 1, wherein said cylinder of carbon dioxide is equipped with a siphon-type delivery system to supply said pressurized carbon dioxide propellant to said disinfectant composition.

16. The method according to claim 15, further comprising heating said pressurized carbon dioxide propellant prior to supplying said pressurized carbon dioxide propellant to said container of said disinfectant composition.

* * * * *